(12) United States Patent
Jordan et al.

(10) Patent No.: US 6,204,220 B1
(45) Date of Patent: Mar. 20, 2001

(54) SUBSTITUTED 2-OXO-3-ALKYNOIC ACIDS AND METHODS OF USE THEREOF

(75) Inventors: Frank Jordan, Chatham; Angela Marie Brown, Teaneck, both of NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/346,086

(22) Filed: Jul. 1, 1999

Related U.S. Application Data
(60) Provisional application No. 60/091,337, filed on Jul. 1, 1998.

(51) Int. Cl.[7] .................................................. A01N 37/06
(52) U.S. Cl. ....................... 504/142; 504/313; 504/314; 504/320; 504/321; 504/325
(58) Field of Search ..................................... 504/314, 313, 504/320, 321, 325, 142

(56) References Cited

PUBLICATIONS

Devine et al. Physiology of Herbicide Action. Chapter 15, "Other Sites of Herbicide Action". NJ: PTR Prentice Hall. p. 323–324, 1993.*

Brown et al. Biochemistry. 36(26):8071–8081. "2–Oxo–3–alkynoic Acids, Universal Mechanism–Based Inactivators of Thiamin Diphosphate–Dependent Decarboxylases: Synthesis and Evidence for Potent Inactivation of the Pyruvate Dehydrogenase Multienzyme Complex", 1997.*

* cited by examiner

*Primary Examiner*—S. Mark Clardy
(74) *Attorney, Agent, or Firm*—Dann Dorfman, Herrell & Skillman

(57) ABSTRACT

Pyruvate acid analogues are provided which have utility as herbicidal agents.

22 Claims, 7 Drawing Sheets

| Common Name | Chemical Name | Common Name | Chemical Name |
|---|---|---|---|
| anilofos | S-4-chloro-N-isopropylcarbaniloyl-methyl-O,O-dimethyl phosphorodithioate | MCPB | 4-(4-chloro-2-methylphenoxy)butanoic acid |
| bensulfuron methyl | 2-[[[[[(4,6-dimethoxy-2-pyrimidinyl) amino]sulfonyl]methyl]-benzoic acid, methyl ester | MON 7200 | S,S-dimethyl-2-(difluoromethyl)-4-(2-methylpropyl)-6-(trifluoromethyl)-3,5-pyridinedicarbothioate |
| benfuresate | 2,3-dihydro-3,3-dimethylbenzofuran-5-yl)ethanesulphonate | mefluidide | N-[2,4-dimethyl-5-[[(trifluoromethyl)sulfonyl]amino]phenyl]-acetamide |
| bentazon | 3-(1-methylethyl)-(1H)-2,1,3-benzothiadiazin-4(3H)-one, 2,2-dioxide | mefenacet | 2-(2-benzothiazolyloxy-N-methyl-N-phenylacetamide |
| benzofluor | N-[4-(ethylthio)-2-(trifluoromethyl) phenyl]methanesulfonamide | methazole | 2-(3,4-dichlorophenyl)-4-methyl-1,2,4-oxadiazolidine-3,5-dione |
| bifenox | methyl 5-(2,4-dichlorophenoxy)-2-nitrobenzoate | metsulfuron methyl | 2-[[[[(4-methoxy-6-methyl-1,3,5-tri-azin-2-yl)amino]carbonyl]-amino]sulfonyl]benzoic acid, methyl ester |
| bromoxynil | 3,5-dibromo-4-hydroxybenzonitrile | | |
| butachlor | N-(butoxymethyl)-2-chloro-N-(2,6-diethylphenyl)acetamide | molinate | S-ethyl hexahydro-1H-azepine-1-carbothioate |
| chlormethoxy-nil | 2,4-dichlorophenyl 4-nitro-3-methoxyphenyl ether | monuron | N'-(4-chlorophenyl)-N,N-dimethylurea |
| chlornitrofen | 2,4,6-trichlorophenyl-4-nitrophenyl ether | nitrofen | 2,4-dichloro-1-(4-nitrophenoxy)-benzene |
| cinmethylin | exo-1-methyl-4-(1-methylethyl)-2-[(2-methylphenyl)methoxy]-7-oxa-bicyclo[2.2.1]heptane | norflurazon | 4-chloro-5-(methylamino)-2-[3-(trifluoromethyl)phenyl]-3(2H)-pyridazinone |
| CGA 142'464 | 3-(4,6-dimethoxy-1,3,5-triazin-2-yl)-1-[2-(2-methoxyethoxy)-phenyl-sulfonyl]-urea | oryzalin | 4-(dipropylamino)-3,5-dinitrobenzene-sulfonamide |
| desmetryn | 2-(isopropylamino)-4-(methylamino)-6-(methylthio)-s-triazine | oxadiazon | 3-[2,4-dichloro-5-(1-methylethoxy)-phenyl]-5-(1,1-dimethylethyl)-1,3,4-oxadiazol-2(3H)-one |
| dichlobenil | 2,6-dichlorobenzonitrile | | |
| dimepiperate | S-1-methyl-1-phenylethylpiperidine-1-carbothioate | oxyfluorfen | 2-chloro-1-(3-ethoxy-4-nitrophenoxy)-4-(trifluoromethyl)benzene |
| dymron | N–(4-methylphenyl)-N'-(1-methyl-1-phenylethyl)urea | pendimethalin | N-(1-ethylpropyl)-3,4-dimethyl-2,6-dinitrobenzenamine |
| esprocarb (SC2957) | S-benzyl-N-ethyl-N-(1,2-dimethyl-propyl)thiolcarbamate | pretilachlor | α.-chloro-2,6-diethyl-N-(2-propoxyethyl)-anetanilide |
| ethofumesate | (±)-2-ethoxy-2,3-dihydro-3,3-dimethyl-5-benzofuranyl methanesulfonate | propanil | N-(3,4-dichlorophenyl)propanamide |
| | | pyrazosulfuron ethyl | ethyl 5-[3-(4,6-dimethoxypyrimidin-2-yl)ureadosulfonyl]-1-methylpyrazole-4-carboxylate |
| fenoxaprop | (±)-2-[4-[(6-chloro-2-benzoxazolyl)-oxy]phenoxy]propanoic acid | pyrazolate | 4-(2,4-dichlorobenzoyl)-1,3-dimethyl-pyrazol-5-yl- -p-toluenesulphonate |
| fluazifop | (±)-2-[4-[[5-(trifluoromethyl)-2-pyridinyl]oxy]phenoxy]propanoic acid | quizalofop ethyl | (±)-2-[4-[(6-chloro-2-quinoxalinyl)-oxy]phenoxy]propanoic acid, ethyl ester |
| fluorodifen | -p-nitrophenyl α,α,α,-trifluoro-2-nitro-p-tolyl ether | quinclorac | 3,7-dichloro-8-quinoline carboxylic acid |
| fomesafen | 5-[2-chloro-4-(trifluoromethyl)-phenoxy]-N-(methylsulfonyl)-2-nitrobenzamide | SK-233 | 1-(αα-dimethylbenzyl)-3-(4-methyl-phenyl)urea |
| | | thiobencarb | S-[(4-chlorophenyl)methyl] diethylcarbamothioate |
| lactofen | (±)-2-ethoxy-1-methyl-2-oxoethyl-5-[2-chloro-4-(trifluoromethyl)-phenoxy]-2-nitrobenzoate | triclopyr | [(3,5,6-trichloro-2-pyridinyl)-oxy]acetic acid |
| | | 2,4-D | (2,4-dichlorophenoxy)acetic acid |
| MCPA | (4-chloro-2-methylphenoxy)acetic acid | 2,4-DB | 4-(2,4-dichlorophenoxy)butanoic acid |
| | | -- | 1-(α,α,-dimethylbenzyl)-3- -p-toluylurea |
| | | -- | 1-α,α-dimethyl-p-methylbenzyl-3- -p'-toluylurea |

Fig. 7

SUBSTITUTED 2-OXO-3-ALKYNOIC ACIDS AND METHODS OF USE THEREOF

This application claims priority under 35 U.S.C. §119(e) from US Provisional Application 60/091,337 filed Jul. 1, 1998, the entire disclosure of which is incorporated by reference herein.

Pursuant to 35 U.S.C. §202(c) it is acknowledged that the U.S. Government has certain rights in the invention described herein, which was made in part with funds from the National Institutes of Health, Grant Number, GM-50380.

FIELD OF THE INVENTION

The present invention relates to the field of herbicides for use in agriculture. More specifically, the invention provides potent irreversible inhibitors of the pyruvate dehydrogenase multienzyme complex and methods of use therof.

BACKGROUND OF THE INVENTION

Several publications are referenced in this application by author name and year of publication in parentheses in order to more fully describe the state of the art to which this invention pertains. The disclosure of each of these publications is incorporated by reference herein.

New compounds effective for controlling the growth of undesired vegetation are in constant demand. In the most common situation, such compounds are sought to selectively control the growth of weeds agronomically, in useful crops, including but not limited to cotton, rice, corn, wheat, and soybeans. Unchecked weed growth in such crops can cause significant losses, reducing profits to the farmer and increasing costs to the consumer.

In other situations, herbicides are desired which will control all plant growth. Examples of areas in which complete control of all vegetation is desired are areas around railroad tracks and industrial storage areas. There are many products commercially available for such purposes, but the search continues for products which are more effective, less costly, and environmentally safe.

SUMMARY OF THE INVENTION

In accordance with the present invention, argriculturally suitable compositions are provided which comprise certain 2-oxoalkynoic acids and derivatives thereof as well as methods of using such compositions as preemergence and/or post emergence herbicides. Representative compounds which are useful for practicing this invention are 2-oxo-3-butynoic acid, 2-oxo-3-pentynoic acid and 2-oxo-3 heptynoic acid. The synthetic scheme for synthesis of these compounds is provided in Example I.

In a preferred embodiment of the invention a herbicidal composition is provided which comprises a herbicidally effective amount of a compound having the formula:

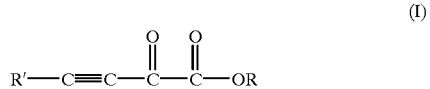

(I)

wherein R represents H or the residue of a protecting group; R' represents R"(CH$_2$)$_n$—, wherein R" is selected from the group consisting of hydrogen or halogen, or R' represents unsubstituted or substituted phenyl (C$_6$H$_5$), wherein the phenyl substituent is at least one selected from the group consisting of fluorine or trifluoromethyl; and n is an integer from 0–4, or an agriculturally suitable salt of the acid form of said compound, and a carrier medium is provided. In formula (I), R may be the residue of an ester protecting group which is cleavable by a plant esterase. Such an ester protecting group may be selected from the group consisting of a benzyloxymethyl ester and a methoxymethyl ester. Furthermore, R may be the residue of an ester protecting group that is photochemically cleavable. Representative of this type of protecting group is a phenyl-substituted phenyacyl ester. In another embodiment, R is the residue of a t-butyl ester protecting group.

The carrier medium comprises an inert liquid diluent and, optionally a surfactant. Preferably the liquid diluent is a solvent for the compound of formula I. Alternatively, the carrier medium may comprise an inert solid diluent.

The herbicidal composition of the invention may further comprise at least one additive selected from the group consisting of anti-foaming agents, anti-caking agents, anti-corrosive agents, anti-bacterial agents and anti-fungal agents. Finally the composition of the invention may include at least one additional herbicide selected from the group set forth in FIG. 7.

In yet another aspect of the invention, a method for controlling the growth of undesired vegetation is provided. The method entails applying an herbicidally effective amount of the compositions of the invention to the site to be protected.

BRIEF DESCRIPTION OF THE DRAWINGS

FIG. 1B. Inactivation of resolved E1 by 2-oxo-3-butynoic acid. Resolved E1 (0.083 mg/mL) was incubated at room temperature in the dark in 20 mM KH$_2$PO$_4$ buffer, pH 7.5, containing 1 mM ThDP and 5 mM MgCl$_2$ with various concentration of 2-oxo-3-butynoic acid in a total volume of 0.5 mL. At different times aliquots of 50 μL were withdrawn and diluted into 1 mL of a reaction mixture containing all components required for assaying the overall reaction and E2–E3 subcomplex. The reaction was initiated by adding CoA. FIG. 1C. and FIG. 1D. Double reciprocal plots of the first-order rate constants and corresponding inhibitor concentrations in FIGS. 1A and 1B, respectively.

FIG. 2A—Effects of ThDP and pyruvate on the inactivation of 3-lip PDHc by 2-oxo-3-heptynoic acid. 3-lip PDHc (0.122 mg/mL) was incubated at room temperature in the dark with 2 mM of 2-oxo-3-heptynoic acid in 20 mM KH$_2$PO$_4$ buffer, pH 7.5 containing: 1 mM ThDP and 5 mM MgCl$_2$ (curve 1); as in curve 1 but no ThDP (curve 2) ; and as in curve 1 with 5 mM pyruvate (curve 3). At different times 50 μL aliquots were withdrawn and diluted into 1 mL of reaction medium for assaying the overall reaction as described in FIG. 1A. FIG. 2B—Effects of ThDP and pyruvate on the inactivation of resolved E1 by 2-oxo-3-butynoic acid. Resolved E1 (0.179 mg/mL) was incubated at room temperature in the dark with 0.12 mM of 2-oxo-3-butynoic acid in 20 mM KH$_2$PO$_4$ buffer, pH 7.5, containing 1 mM ThDP, 5 mM MgCl$_2$ (curve 1); as in curve 1 but no ThDP (curve 2); as in curve 1 with 5 mM pyruvate (curve 3). Reaction conditions were the same as in FIG. 1A.

FIG. 4A—Effect of 2-oxo-3-butynoic acid on the fluorescence emission spectrum of resolved E1. The fluorescence emission spectrum of resolved E1 (0.173 mg/mL) in 3 mL of 20 mM $KH_2PO_4$ buffer, pH 7.5, containing: 1 mM $MgCl_2$ (curve 1); 1 mM $MgCl_2$ and 0.2 mM ThDP (curve 2); and at different times after adding 0.11 mM 2-oxo-3-butynoic acid to (2), curve number in parentheses: 1 min (3), 4 min (4), 7 min (5), 10 min (6), 20 min (7), 32 min (8). The excitation wavelength was 295 nm. FIG. 4B—Effect of 2-oxo-3-butynoic acid on the fluorescence emission spectrum of resolved apo-E1 in the absence of ThDP and Mg $Cl_2$. The fluorescence emission spectrum of resolved E1 (0.173 mg/mL) in 3 mL of 20 mM $KH_2PO_4$ buffer, pH 7.5 (curve 1); with 0.11 mM of 2-oxo-3-butynoic acid at different times (curve number in parentheses): 4 min (2); 7 min (3); 15 min (4); 20 (5,6); and 30 min (5,6). The excitation wavelength was 295 nm. The inset shows the dependence of relative fluorescence ($F_t/F_o$) *100 at 335 nm on time of incubation, where $F_o$ is the fluorescence intensity of E1 in the absence of 2-oxo-3-butynoic acid; $F_t$ is the fluorescence intensity of E1 in the presence of 0.11 mM of 2-oxo-3-butynoic acid at the indicated time of incubation.

FIG. 5A—Effect of DTT on the inactivation of resolved E1 by 2-oxo-3-butynoic acid. The resolved E1 (0.173 mg/mL) in 20 mM $KH_2PO_4$ buffer, pH 7.5, containing 1 mM ThDP, 5 mM $MgCl_2$ at room temperature was incubated with 0.5 mM of 2-oxo-3-butynoic acid in the dark in a total volume of 0.5 mL in the absence (curve 1) or in the presence of 5 mM DTT (curve 2). At different times of incubation, aliquots were withdrawn and the activity was measured in the overall reaction as described in FIG. 1B. FIG. 5B—Attempted rescue with hydroxylamine of resolved E1 inactivated by 2-oxo-3-butynoic acid. The resolved E1 (0.173 mg/mL) in 20 mM $KH_2PO_4$ buffer, pH 7.5, containing 1 mM ThDP, 5 mM $MgCl_2$ was incubated for 20 min with 0.5 mM of 2-oxo-3-butynoic acid in a volume of 0.5 mL in the dark. After about 68% inhibition was reached, 0.5 M hydroxylamine was added and the activity was measured during the next 100 min as described in FIG. 1B.

FIG. 7. A list of common herbicides is shown which may be used in combination with the herbicidal compounds of the present invention.

DETAILED DESCRIPTION OF THE INVENTION

Figure 1:
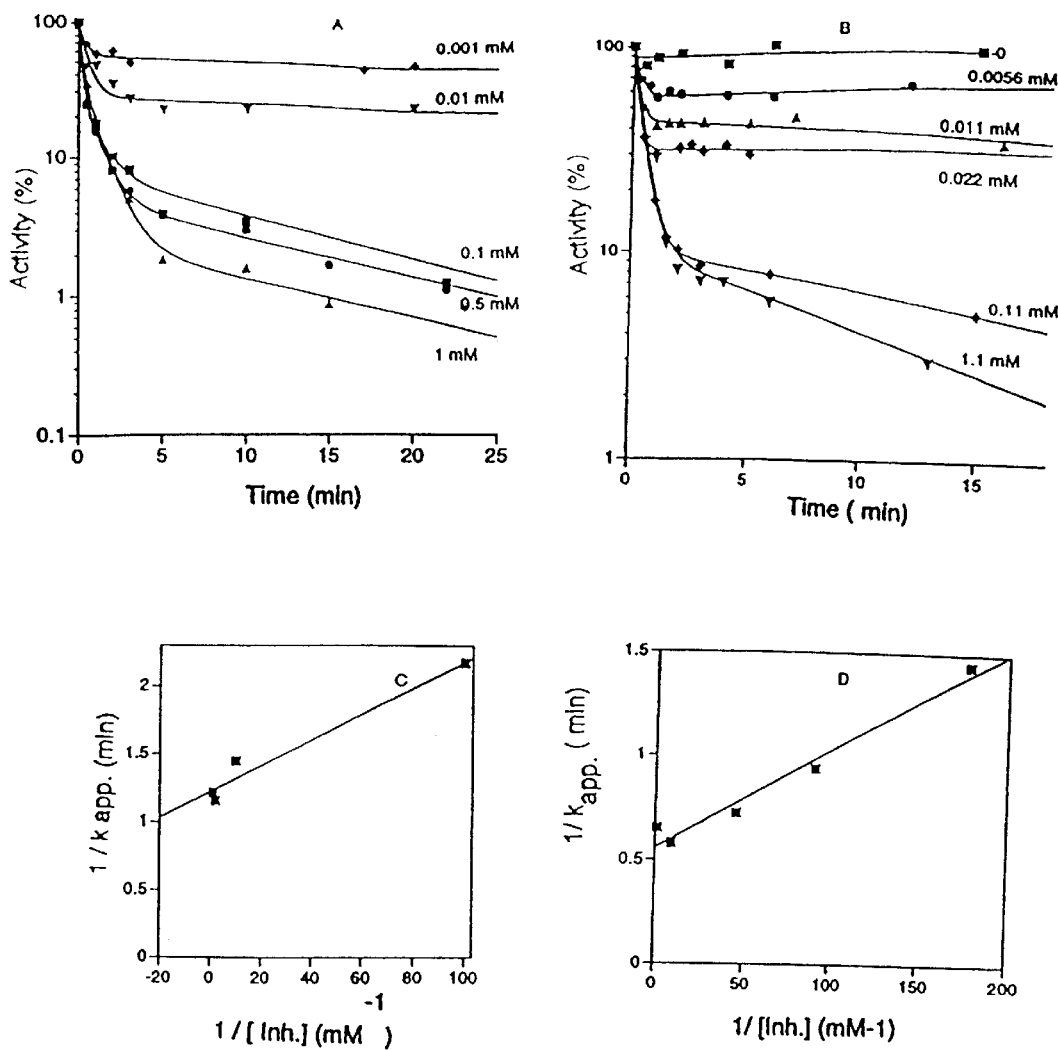
FIG. 1. Inactivation of 1-lip PDHc by 2-oxo-3-butynoic acid. 1-lip PDHc (0.157 mg/mL) was incubated in the dark at room temperature in 20 mM KH$_2$PO$_4$ buffer, pH 7.5, containing 1 mM ThDP and 5 mM MgCl$_2$ with the indicated concentrations of 2-oxo-3-butynoic acid in a total volume of 0.5 mL. At different times aliquots of 50 μL were withdrawn and diluted into 1 mL of a reaction mixture containing all components required for assaying the overall reaction. The reaction was initiated by adding CoA.

Enzymes that utilize thiamin diphosphate (ThDP) to facilitate the decarboxylation of 2-oxoacids include, in order of increasing complexity: pyruvate decarboxylase (PDC, EC 4.1.1.1) which performs a non-oxidative decarboxylation yielding acetaldehyde; pyruvate oxidase (POX, EC 1.2.3.3) which requires FAD as an additional cofactor and yields acetate in *E. coli* and acetylphosphate in *Lactobacillus plantarum*; and the prokaryotic and eukaryotic pyruvate dehydrogenase multienzyme complexes (PDHc) which produce acetyl-CoA. PDHc catalyzes the oxidative decarboxylation of pyruvate in the following overall reaction (Koike et al., 1960):

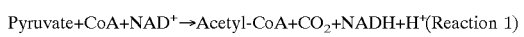

Pyruvate+CoA+NAD$^+$→Acetyl-CoA+$CO_2$+NADH+H$^+$ (Reaction 1)

In *E. coli* three different enzyme components are involved in the above reaction: pyruvate dehydrogenase (EC 1.2.4.1; E1) utilizing thiamin diphosphate (ThDP) as a cofactor; dihydrolipoamide acetyltransferase (EC 2.3.1.12; E2), which contains covalently-bound lipoyl groups; and lipoamide dehydrogenase (EC 1.8.1.4; E3), containing tightly bound FAD. The multienzyme complex performs the following series of reactions (Gunsalus, 1954; Massey, 1963; Reed, 1974):

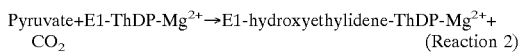

Pyruvate+E1-ThDP-Mg$^{2+}$→E1-hydroxyethylidene-ThDP-Mg$^{2+}$+ $CO_2$ (Reaction 2)

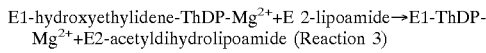

E1-hydroxyethylidene-ThDP-Mg$^{2+}$+E 2-lipoamide→E1-ThDP-Mg$^{2+}$+E2-acetyldihydrolipoamide (Reaction 3)

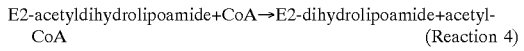

E2-acetyldihydrolipoamide+CoA→E2-dihydrolipoamide+acetyl-CoA (Reaction 4)

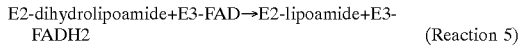

E2-dihydrolipoamide+E3-FAD→E2-lipoamide+E3-FADH2 (Reaction 5)

E3-FADH2+NAD+→E3-FAD+NADH (Reaction 6)

The *E. coli* complex consists of multiple copies of each component, an ideal polypeptide stoichiometry being: 24 E1, molecular weight 99,474 (Stephens et al., 1983a), 24 E2 molecular weight 65,959 (Stephens et al., 1983b); and 12 E3, molecular weight 50,554 (Stephens et al, 1983c); which corresponds to a total calculated molecular weight of 4.57× 10$^6$ Daltons.

Metabolic inhibitors of PDHc include reduced nicotinamide adenine dinucleotide (NADH), acetyl-CoA, and guanosine triphosphate (GTP) (Bremer, 1969; Schwartz et al., 1968; Schwartz & Reed, 1970; Bisswanger & Henning, 1971). Mammalian PDHc is regulated in a more complex fashion by phosphorylation and dephosphorylation (Reed, 1974) of the alpha subunit of the tetrameric E1 component (a2a2). PDHc from *E. coli* is also inhibited by various substrate analogs including bromopyruvate (Lowe & Perham, 1984), fluoropyruvate (Bisswanger, 1980; Flournoy & Frey, 1989), the phosphonate (Kluger & Pike, 1977) and phosphinate analogs of pyruvate (Schonbrunn-Hanebeck et al., 1990), mono and bifunctional arsenoxides (Stevenson et al., 1978; Adamson & Stevenson, 1981; Adamson et al., 1984), branched-chain 2-oxoacids (Jackson & Singer, 1983), and the coenzyme analogs tetrahydrothiamin diphosphate (Maldonado et al., 1972; Apfel et al., 1984; Lowe et al., 1983) and the 2-thiazolone and 2-thiothiazolone analogs of ThDP (Gutowski & Lienhard, 1976). In this lab, McNally generated a panel of monoclonal antibodies to PDHC from *E. coli*, one of which gave better than 98% inhibition of both holo-PDHc and of the resolved E1 subunit (McNally et al., 1995; and unpublished). PDC is only weakly inhibited by halopyruvates, and acetylphosphinate is also a weak inhibitor (Spinka & Hüabner, 1996). Inhibition of PDC by thiamin analogs is difficult to study, since the coenzyme is tightly bound and can only be fully substituted with virtual destruction of the tetrameric structure.

In earlier studies, we had reported that 2-oxo-4-phenyl-3-butenoic acids with a variety of substituents on the phenyl ring inhibit PDC (Kuo & Jordan, 1983; Jordan et al., 1986; Annan, Paris & Jordan, 1989; Zeng et al., 1991; Menon-Rudolph et al., 1992), while others attempted unsuccessfully to inhibit POX and PDHC with this group of compounds. Recently, Chiu developed a method for the synthesis of 2-oxo-4-phenyl-3-butynoic acid and showed that the compound is a mechanism-based inactivator of PDC, that is converted to cis and trans cinnamic acids, rather than to 3-phenyl-2-propynal, the expected product of decarboxylation (Chiu & Jordan, 1994). Based on Zeng's discovery of the "misprotonation" of the allylic enamine/2-$\alpha$-carbanion derived from the decarboxylation of 2-oxo-4-phenyl-3-butenoic acids, the results could be explained in a parallel fashion, so that a 2-acyl-ThDP is produced that is not readily released from the active center of the enzyme. [RC=CCOCOOH, where R=H—, $CH_3$—, $CH_3CH_2CH_2$— and $C_6H_5$— are 2-oxo-3-butynoic, 2-oxo-3-pentynoic, 2-oxo-3-heptynoic and 2-oxo-4-phenyl-3-butynoic acid, respectively.]

When 2-oxo-4-phenyl-3-butynoic acid was incubated with PDHc from *E. coli*, no inhibition resulted. In order to test whether such 2-oxo-3-alkynoic acids hold promise as inhibitors of other ThDP-dependent decarboxylases, aliphatic analogs, 4-, 5- and 7-carbon molecules in length were synthesized. The 4-carbon compound is the shortest, parent compound. Herein is reported the synthesis of, and preliminary kinetic studies with, these compounds. The results reported herein reveal that 2-oxo-3-butynoic acid irreversibly inactivates all of the following: PDC from *Saccharomyces cerevisiae*, POX from *Lactobacillus plantarum* and PDHc from *E. coli*. The 5-carbon and 7-carbon analogs also inhibit PDC and POX.

In order to enhance the stability of the compounds of the invention, it may be necessary to protect certain moieties with protecting groups. Suitable reagents for this purpose include tertiary butyl ester, esters cleavable by esterases within plants, including but not limited to benzyloxymethyl and methoxymethyl esters, and esters that may be cleaved photochemically by sunlight, such as phenyl-substituted phenacyl esters.

FORMULATIONS AND CARRIER MEDIA

Useful formulations of the invention can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1%–99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE A

| Surfactant(s) | Active Ingredient | Weight Percent* Diluent(s) | |
|---|---|---|---|
| Wettable Powders | 20–90 | 0–74 | 1–10 |
| Oil Suspensions, Emulsions, Solutions, (Including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active Ingredient plus at least one of a Surfactant or a Diluent equals 100 weight percent.

Lower or higher levels of active ingredients can, of course, be present depending on the intended use and physical properties of the compound. Higher ratios of surfactant to active ingredient are sometimes desirable, and are achieved by incorporation into the formulation or by tank mixing.

Typical solid diluents are described in Watkins et al. "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

MATERIALS AND METHODS

Solutions were concentrated in vacuo using a rotary evaporator. Organic solvents were dried. The organic layers were dried over $MgSO_4$. NMR spectra were obtained on a Varian VXR-400 MHz instrument. Infra-red spectra were obtained using a Mattson Polaris™ spectrometer. Elemental analyses were done at Robertson Microlit, Madison, N.J.

Synthesis

Monoethyloxalic acid-N-methoxy-N-methylamide. To a stirred solution of N,O-dimethylhydroxylamine hydrochloride (3.00 g, 30.9 mmol) and ethyl oxalyl chloride (1.2 equiv., 5.07 g, 37.1 mmol) in dry $CH_2Cl_2$ (60 mL), was added $Et_3N$ (2.0 equiv., 6.21 g) dropwise at 0° C. The reaction mixture was stirred at room temperature for 30 min then methanol (10 mL) was added to quench the reaction. After concentration to dryness precipitation was induced by the addition of dry THF (20 mL) and the white salt was filtered and washed with dry THF (10 mL). The combined THF layer was then concentrated to a yellow oil that was purified by vacuum distillation to furnish 4.08 g (82%) of the amide as a yellow oil. $^1$H NMR ($CDCl_3$/TMS) δ 1.34 (t, 3, J=7 Hz), 3.48 (s, 3), 3.78 (s, 3), 4.31 (q, 2, J=7 Hz); $^{13}$C NMR ($CDCl_3$/TMS) δ 14.0, 31.4, 62.1, 62.3, 162.2, 162.6.

Ethyl 2-oxo-3-heptynoate. A solution of 1-pentyne (341 g, 0.5 mL, 5.0 mmol) in dry THF (15 mL) at −78° C. was treated dropwise with n-BuLi (1.6 M, 3.12 mL). The mixture was stirred for 60 min then added to a solution of monoethyloxalic acid-N-methoxy-N-methylamide (0.805 g, 5.0 mmol) in 30 mL of dry THF that had been cooled to −78° C. After 45 min, the reaction mixture was poured into cold 20% $H_3PO_4$/ether (50 mL/50 mL). The aqueous layer was separated and extracted with ether. The combined ether layer was next washed with 10% $H_3PO_4$ then dried and concentrated. Flash chromatography (pet. ether/EtOAc, 95:5) yielded the pure 2-oxo ester (0.601 g, 72%) as a pale yellow oil. $^1$H NMR ($CDCl_3$/TMS) δ 4.36 (q, 2, J=7 Hz), 1.06 (t, 3, J=7 Hz), 1.39 (t, 3, J=7 Hz), 1.67 (m, 2, J=7 Hz), 2.47 (t, 2, J=7 Hz); $^{13}$C NMR ($CDCl_3$/TMS) δ 170, 159.5, 102.4, 80.3, 21.5, 22.0, 13.3, 14.0, 64.0; IR (neat) 2968, 2877, 2212, 1763, 1685 cm$^{-1}$. Elemental analysis: Calcd. C, 64.27, H, 7.19; Found C, 65.08, H, 7.28.

Ethyl 2-oxo-3-pentynoate. To a solution of monoethyloxalic acid-N-methoxy-N-methylamide (0.805 g, 5.0 mmol) in THF (20 mL) at −78° C. was added dropwise 1-propynyl-magnesium bromide (10 mL, 0.5 M in THF from Aldrich). The mixture was stirred for 3 h while the temperature rose to 25° C. The reaction mixture was then poured into an ice-cold solution of 20% $H_3PO_4$/ether (2:1). The aqueous layer was separated and extracted with ether. The combined ether layers were washed with 10% $H_3PO_4$, then dried and concentrated. Flash chromatography (pet. ether/EtOAc, 9:1) yielded the pure 2-oxo ester as a pale yellow liquid. $^1$H NMR ($CDCl_3$/TMS) δ 1.39 (t, 3, J=7 Hz), 2.17 (s,3), 4.36 (q, 2, J=7 Hz); $^{13}$C NMR ($CDCl_3$/TMS) δ 170.0, 160.4, 101.2, 81.0, 64.8, 14.3, 4.3; IR (neat) 2982, 2878, 2218, 1786, 1678 cm$^{-1}$. Elemental analysis: Calcd. C, 59.98, H, 5.76; Found C, 60.35, H, 5.77.

Ethyl 2-oxo-3-butynoate. To a solution of monoethyloxalic acid-N-methoxy-N-methylamide (0.805 g, 5.0 mmol) in THF (20 mL) at −78° C. was added dropwise ethynyl-magnesium bromide (10 mL, 0.5 M in THF from Aldrich). The mixture was stirred for 3 h while the temperature rose to 25° C. The reaction mixture was then poured into an ice-cold solution of 20% $H_3PO_4$/ether (2:1). The aqueous layer was separated and extracted with ether. The combined ether layers were washed with 10% $H_3PO_4$, then dried and concentrated. Flash chromatography (pet. ether/EtOAc, 9:1) yielded the pure 2-oxo ester as a colorless liquid. $^1$H NMR ($CDCl_3$/TMS) δ 1.39 (t, 3, J=7 Hz), 3.64 (s,1), 4.36 (q, 2, J=7 Hz); $^{13}$C NMR ($CDCl_3$/TMS) δ 169.4, 158.7, 85.4, 79.8, 64.3, 14.9; IR (neat) 2962, 2876, 2220, 1726, 1602 cm$^{-1}$. Elemental analysis: Calcd. C, 57.16, H, 4.80; Found C, 56.19, H, 5.10.

2-Oxo-3-heptynoic acid. To a solution containing ethyl 2-oxo-3-heptynoate (0.500 g, 3.02 mmol) and THF: MeOH : $H_2O$ (1:1:2, 15 mL) at room temperature, aqueous NaOH (0.5 M) was added dropwise while stirring. The pH was never allowed to exceed pH 8. The addition of NaOH was stopped after an equivalent amount had been added or when the increase in pH became very slow. The organic solvents were removed in vacuo and the pH of the aqueous remainder was adjusted to 1.0 with conc. $H_2SO_4$ and extracted with ether (3×15 mL). The combined ether layers were dried and concentrated to yield the acid (0.312 g, 74%) as a dark yellow liquid.

$^1$H NMR ($CDCl_3$/TMS) δ 1.06 (t, 3, J=7 Hz), 1.70 (m, 2, J=7 Hz) 2.28 (t, 2, J=7 Hz).

2-Oxo-3-pentynoic acid (synthesized as the 7-carbon acid) gave:

$^1$H NMR ($CDCl_3$/TMS) δ 2.20 (s, 3); $^{13}$C NMR ($CDCl_3$/TMS) δ 170.0, 159.6, 102.0, 79.8, 14.8.

2-Oxo-3-butynoic acid (synthesized as the 7-carbon acid) gave:

$^1$H NMR($CDCl_3$/TMS) δ 3.5 (s, 1 H); $^{13}$C NMR ($CDCl_3$/TMS) δ 171.5, 160.0, 86.8,80.0; IR ($CCl_4$) 3500, 3279, 2098, 1734, 1695 cm$^{-1}$.

Enzyme purification and assays.

Pyruvate decarboxylase from *Saccharomyces cerevisiae* was overexpressed in *E. coli* (Baburina et al., 1994), then purified according to Farrenkopf & Jordan (1992). It was assayed spectrophotometrically by coupling to alcohol dehydrogenase (Holzer et al., 1960).

Pyruvate oxidase from *Lactobacillus plantarum* was a gift from Boehringer Mannheim and was assayed according to the manufacturer's instructions at 25° C. by measuring the rate of 4-quinonimine production from $H_2O_2$, 3,5-dichlorophenolsulfonic acid and 4-aminoantipyrine in the presence of horseradish peroxidase, at 546 nm, using a Cobas-Bio (Roche Diagnostics, Somerville, N.J.) automated centrifugal analyzer. The assay reaction mixture (total vol. 0.25 mL) contained: 40 mM sodium pyruvate; 50 mM potassium phosphate buffer, pH 6.5 with 10% (v/v) glycerol; 6.8 mM 3,5-dichlorophenolsulfonic acid; 0.03% of 4-aminoantipyrine; and 5u/mL of horseradish peroxidase. The reaction was initiated by adding POX.

Bacterial strains and plasmids for PDHc. Derivatives of the PDHc null strain, *E. coli* JRG1342 contained $P_{tac}$ expression plasmids encoding PDHc with E2 chains bearing three lipoyl domains (3-lip PDHc; pGS523, the wild type parental complex), or a single lipoyl domain in each E2 subunit (1-lip PDHc; pGS501), and variant 1-lip PDH complexes with mutations in the E1 gene leading to C259S (pGS457) and C259N (pGS596) substitutions (Machado et al., 1992; Machado, 1993).

Purification of PDHc. Cultures for purification of 1-lip and 3-lip PDH complexes were grown at 37° C. in LB medium containing glucose (0.2%) and ampicillin (50

μg/mL). The PDH complexes were induced by adding IPTG to 60 μM as described by Russell et al. (1992). Cells were disrupted by ultrasonic treatment after preincubation with lysozyme (0.6 mg/mL final concentration) for 15 min. The PDHc was sedimented by ultracentrifugation (100,000×g for 3 h) and further purified by chromatography on a Sephacryl S-400 HR column. Fractions containing PDHc were pooled and treated with ammonium sulfate to 70% saturation. The enzyme was dissolved in buffer A (20 mM potassium phosphate, pH 7.8, 2 mM $Na_2EDTA$, 1 mM PMSF, and 1 mM benzamidine.HCl) then dialyzed against the same buffer. The PDH complexes were stored in buffer A at −20° C.

Resolution of the E1 component from PDHc. E1 was resolved from the PDHc on a Sepharose CL-6B (1.5×100 cm) column under alkaline conditions. PDHc was dialyzed against 50 mM Tris buffer, pH 9.0, containing 0.1 mM benzamidine.HCl, 0.15 M NaCl, 0.1 mM PMSF for 2 h, before applying to a column equilibrated and eluted with the same buffer. Analysis by SDS-PAGE revealed that the first peak to emerge is the E2–E3 sub-complex, followed by E1 containing a trace amount of E3. E1 from the parental 3-lip and 1-lip PDH complexes was also separated from the other subunits using a Thiol-Sepharose 4B affinity column (2.5× 20 cm) under conditions described for resolution of E1 from PDHc isolated from *Azotobacter vinelandii* (de Graaf-Hess & de Kok, 1982).

Activity and related measurements on PDHc. The overall enzymatic reaction of the PDH complex was assayed using a Varian DMS 300 spectrophotometer or the Cobas Bio (Roche Diagnostics, Somerville, N.J.) automated centrifugal analyzer, monitoring the pyruvate-dependent reduction of $NAD^+$ at 340 nm. The reaction medium contained in 1 mL (DMS 300) or 0.25 mL (Cobas-Bio) test volume: 0.1 M Tris-HCl, pH 8.0; 1 mM $MgCl_2$; 2 mM sodium pyruvate; 2.5 mM $NAD^+$; 0.052–0.2 mM coenzyme A; 0.2 mM ThDP; and 2.6 mM DTT at 27° C. The reaction was initiated either by adding enzyme to a mixture of all other components, or by adding CoA.

One unit of activity is defined as the amount of NADH produced (μmol) per min per mg protein. The activity of resolved E1 was measured after reconstitution with excess E2–E3 subcomplex using the NADH assay for PDHc activity.

Assay for the non-oxidative formation of acetoin and acetolactate by resolved E1. The reaction mixture contained in 0.8 mL of 50 mM $KH_2PO_4$ buffer, pH 7.5: ThDP (1 mM); $MgCl_2$ (2 mM); pyruvate (2 mM) and resolved E1 (0.04–0.1 mg). After 2 h at 37° C. the reaction was stopped by the addition of either 0.1 mL of 2.5 N NaOH (acetoin assay), or 0.02 mL of 6 N HCl (acetolactate assay), according to Kuwana et al. (1968). Tubes for acetolactate measurement were incubated for an additional 2 h at 37° C. to decarboxylate the acetolactate to acetoin. Acetoin was determined according to Westerfeld (1945). The activity is defined as nmoles of acetoin formed per min per mg protein.

Inactivation of 1-lip and 3-lip PDH complexes and resolved E1 component by 2-oxo-3-alkynoic acids. Intact 1-lip or 3-lip PDH complexes (0.050–0.1 mg) or resolved E1 component (0.05–0.09 mg) were incubated in the dark with 5 mM $MgCl_2$, 1 mM ThDP and different concentrations of 2-oxo-3-alkynoic acids in 20 mM $KH_2PO_4$ buffer, pH 7.5 at room temperature in a total volume 0.5 mL. The initial activity (100%) was assayed prior to the addition of 2-oxo-3-alkynoic acids. Samples (50 μL) were withdrawn periodically and diluted into 1 mL of assay solution, containing all components necessary for assay of the overall activity. The activity of untreated enzyme was stable during the time of inactivation.

Quantification of the fraction of sulfhydryl groups in E1 modified by 2-oxo-3-butynoic acid. The concentration of titratable sulfhydryl groups was determined by treating samples (1 mL) containing E1 ($3.02 \times 10^{-6}$ M) in 0.05 M $KH_2PO_4$ buffer, pH 8.0 and 8 M urea, with small aliquots of 5,5'-dithiobis-(2-nitrobenzoic acid) from a 1 mM stock solution, and comparing the absorbencies at 412 nm with those obtained with freshly prepared cysteine solutions in the range $10 \times 10^{-6} - 50 \times 10^{-6}$ M. Protein concentrations were determined by the Bio-Rad method with bovine serum albumin as standard.

Fluorescence measurements on the binding of 2-oxo-3-butynoic acid to E1. The fluorescence spectrum of apo-E1 (enzyme having no activity in the absence of ThDP) was measured using the SLM8100 spectrofluorimeter at 25° C. The excitation wavelength was 295 nm and the emission spectrum, presumably due to tryptophan, was recorded in the 300–450 nm range in a 1 mL or 3 mL quartz cuvette. The concentration of apo-E1 was 0.05–0.175 mg/mL in 20 mM $KH_2PO_4$ buffer, pH 7.5. The excitation and emission monochromator slit widths were 4 nm. The V.3.0 software and KaleidaGraph computer program were used for data processing. The emission maximum for tryptophan ($\lambda$=335 nm) was determined by fitting the points from the peak using the KaleidaGraph computer program.

The Michaelis-Menten constants ($K_m$) for native PDHc and PDHc treated with 2-oxo-3-butynoic acid and 2-oxo-3-heptynoic acid were obtained by fitting steady-state rates at different pyruvate concentrations to the Hill equation and the logarithmic form of the Hill equation using the Delta Graph (Pro4) computer program.

EXAMPLE I

Kinetics of inactivation of 1-lip and 3-lip PDH complexes and resolved E1 in the presence of 2-oxo-3-alkynoic acids. Three analogs of pyruvate were tested as potential inhibitors of the PDHc and resolved E1: 2-oxo-3-butynoic acid; 2-oxo-3-pentynoic acid; and 2-oxo-3-heptynoic acid. Incubation in the presence of saturating ThDP (1 mM) and $MgCl_2$ (5 mM) with any of the three compounds led to the loss of overall activity in a time- and concentration-dependent fashion. The plots of remaining activity versus time were biphasic: a rapid phase of inactivation was followed either by a slow phase at high concentrations of inhibitor or a plateau at low concentrations of inhibitor, as shown for 1-lip PDHc and resolved E1 with 2-oxo-3-butynoic acid in FIGS. 1A and 1B. The biphasic kinetics may be due to chemical instability of the inhibitors, especially 2-oxo-3-butynoic acid. This possibility was excluded because incubating 2-oxo-3-butynoic acid (1 mM) at room temperature in 20 mM $KH_2PO_4$ buffer, pH 7.5 in the presence of 1 mM ThDP and 5 mM $MgCl_2$ for different periods up to 28 min had no significant effect on its ability to inactivate 1-lip PDHc. When a fresh portion of 2-oxo-3-butynoic acid was added to PDHc whose activity had plateaued at about 30%, the activity rapidly declined to a new plateau at 6–8% of the original activity. In contrast, the PDHc activity continued to decline at a low rate when fresh 1-lip PDHc was added to the sample that had already declined to 30% (data not shown). These experiments suggest that the concentration of 2-oxo-3-butynoic acid falls during the inactivation, possibly due to non-specific interaction with the enzyme, or to enzyme-catalyzed decomposition, although none of the pyruvate analogs generated NADH in the overall assay.

The efficacies of the three inhibitors were compared by calculating the apparent rate constants ($k_{app}$) for inactivation from the initial linear slopes of the relationship between the residual activity [log (A_t/A_o)] against time (t). A plot of $k_{app}$ versus [inhibitor] was hyperbolic, suggesting that the enzyme is saturated with the inhibitor, and $k_{app}=k_i/\{1+(K_i/[I])\}$ (Kitz & Wilson, 1962) according to

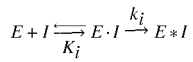

where E*I is inactive enzyme, $k_i$ is the first-order rate constant for conversion of the reversibly formed complex E•I to irreversibly inactivated enzyme at saturating inhibitor concentration, $K_i$ is the dissociation constant for the initial reversibly formed complex, and $k_i/K_i$ is the second-order rate constant for inactivation, a convenient measure of the relative inhibitory efficacy of different compounds.

A total of 5–10 different concentrations of each compound were used to obtain $k_{app}$. The kinetic parameters calculated on the basis of equation (1) are presented in Table 1. It is clear that 2-oxo-3-butynoic acid is by far the most effective inhibitor tested, the second-order inactivation rate constant $(k_i/K_i)$ being 104 mM$^{-1}$ min$^{-1}$, compared to 1.52 and 0.17 mM$^{-1}$ min$^{-1}$ for alkyl chains with 5 and 7 carbons (respectively). The $K_i$ obtained for 2-oxo-3-butynoic acid is 7.9 μM, compared to the $K_m$=0.22 mM for pyruvate, suggesting that the inhibitor forms a stable adduct with the enzyme.

TABLE I

KINETIC DATA FOR THE INHIBITION OF PDHc AND RESOLVED E1 BY 2-OXO-3-ALKYNOIC ACIDS RELATIVE TO FLUOROPYRUVATE[a]

| compound | $k_i$(min$^{-1}$) PDHc | $k_i$(min$^{-1}$) E1 | $K_i$(nM) PDHc | $K_i$(nM) E1 | $k_i/K_i$ (mM · min)$^{-1}$ PDHc | $k_i/K_i$ (mM · min)$^{-1}$ E1 |
|---|---|---|---|---|---|---|
| 2-oxo-heptynoic acid | 0.487 | | 2.850 | | 0.17 | |
| 2-oxo-pentynoic acid | 0.420 | | 0.276 | | 1.52 | |
| 2-oxo-butynoic acid | 0.819 | 1.79 | 0.0079 | 0.0085 | 104.0 | 210.0 |
| fluropyruvic acid[b] | 0.331 | 0.36 | 0.033 | 0.028 | 13.0 | |

[a] $k_i$ is the rate constant for conversion of reversible complex to irreversibly inactivated enzyme at saturating inhibitor concentrations; $K_i$ is the dissociation constant for initial reversible complex; $k_i/K_i$ is the second-order rate constant for inactivation.
[b] Calculated from data reported by Flournoy and Frey (1989).

In the presence of high concentrations of 2-oxo-3-butynoic acid, after a rapid, initial kinetic phase for inactivation there followed a second, slower phase (FIGS. 1A and 1B), rather than the plateau levels observed at low inhibitor concentrations, suggesting that the mechanism of inactivation is perhaps more complex than that presented by equation 1 for the first fast phase of inactivation and includes some additional step/steps prior to the formation of the inactive E*•I complex. The $k_{app}$ calculated for the slow phase of inactivation of 1-lip PDHc and resolved E1 by 2-oxo-3-butynoic acid (FIGS. 1A and 1B) did not significantly vary with the concentration of inhibitor, as illustrated with the following rate constants (in parenthesis is shown the concentration of 2-oxo-3-butynoic acid): 0.062 min$^{-1}$ (0.1 mM); 0.053 min$^{-1}$ (0.5 mM) and 0.056 min$^{-1}$ (1.0 mM) for the 1-lip PDHc, with 0.039 min$^{-1}$ (0.11 mM) and 0.078 min$^{-1}$ (1.1 mM) for resolved E1. Therefore, it is unlikely that the biphasic kinetics of inactivation is a result of two types of residues reacting at different rates with the inhibitor.

For inactivation of 3-lip PDHc by 2-oxo-3-heptynoic acid in the concentration range of 0.35–2.0 mM, the rapid phase of inactivation was followed by a plateau level, whereas with 2-oxo-3-pentynoic acid the slow phase of inactivation was not in evidence in the 0.015–1.5 mM concentration range. At higher concentrations of inhibitor the slower phase was in evidence yielding $k_{app}$ of inactivation of 0.048 min$^{-1}$ (at 3 mM) and 0.022 min$^{-1}$ (at 4 mM), independent of inhibitor concentration, as found with 2-oxo-3-butynoic acid, and suggesting that the slow phase of inactivation may reflect a more complex fate of the inhibitor.

When the E2–E3 subcomplex was preincubated for different times (up to 20 min) with 2-oxo-3-butynoic acid, followed by dilution into a reaction mixture containing all components of the PDHc assay including unmodified E1 component, 100% of the activity could be reconstituted. In contrast, when resolved E1 was treated with inhibitors for different time periods before reconstitution with unmodified E2–E3 complex, a time-dependent decrease in the overall activity was observed (see FIG. 1B for resolved E1 reacted with 2-oxo-3-butynoic acid). Comparing the kinetic constants for inactivation of PDHc and resolved E1 with 2-oxo-3-butynoic acid suggests that the E1 component is even more sensitive to inactivation than the PDH complex (Table 1).

2-Oxo-3-butynoic acid also significantly reduced the formation of non-oxidative decarboxylation products, acetoin and acetolactate by resolved E1 (Table 2). The resolved E1 with 11.5% overall activity remaining produced 30% of the acetoin and 36% of the acetolactate compared to the amounts formed without inactivation. This experiment further confirms that all the inhibitory effects are due to inactivation of the E1 component.

TABLE II

Effects of 2-oxo-3-butynoic acid on acetoin and acetolactate production by resolved E1.

| Extent of inhibition | Pyruvate:NAD$^+$- oxido- reductase reaction[a] (μmol/min/mg protein) | Acetoin production (nmol/min/mg protein) | Acetolactate production (nmol/min/mg protein) |
|---|---|---|---|
| E1 (A$_t$ = 100%) | 2.980 ± 0.420 | 5.17 ± 0.17(100%) | 1.43 ± 0.083(100%) |
| E1A$_t$ = 11.5%)[b] | 0.343 ± 0.023 | 1.52 ± 0.08(30%) | 0.51 ± 0.083(36%) |

[a] The E1 activity was measured in the overall reaction after reconstitution with an excess of E2-E3 subcomplex.
[b] E1 (1.5 mg/mL) in 20 mM KH$_2$PO$_4$ buffer, pH 7.5, containing 0.1 mM ThDP, 1 mM MgCl$_2$ at room temperature in a total volume 0.8 mL, was reacted with 3.7 mM of 2-oxo-3-butynoic acid. Once the activity diminished to 16%, the enzyme was chromatographed on G-25 column (PD-2, Pharmacia) to exclude excess inhibitor. Resolved E1 with a residual activity in the overall reaction of 11.5% was used to measure the non-oxidative activity.

Figure 2:
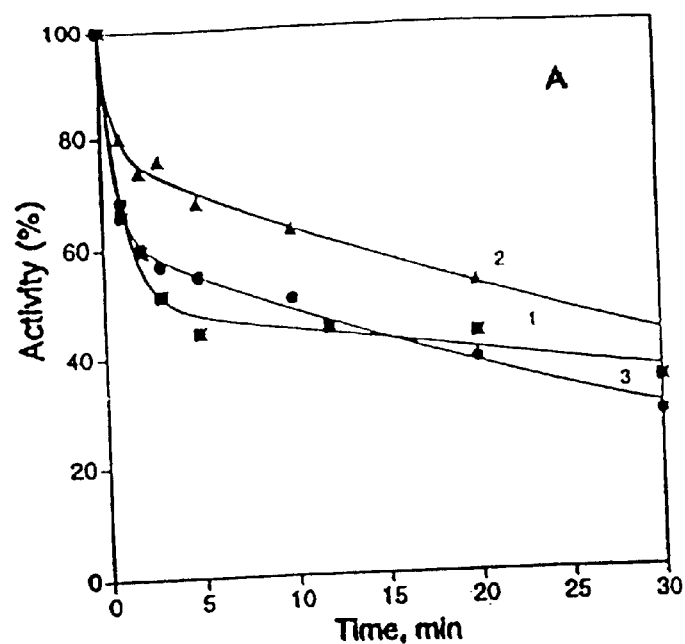
FIG. 2.
Figure 2:
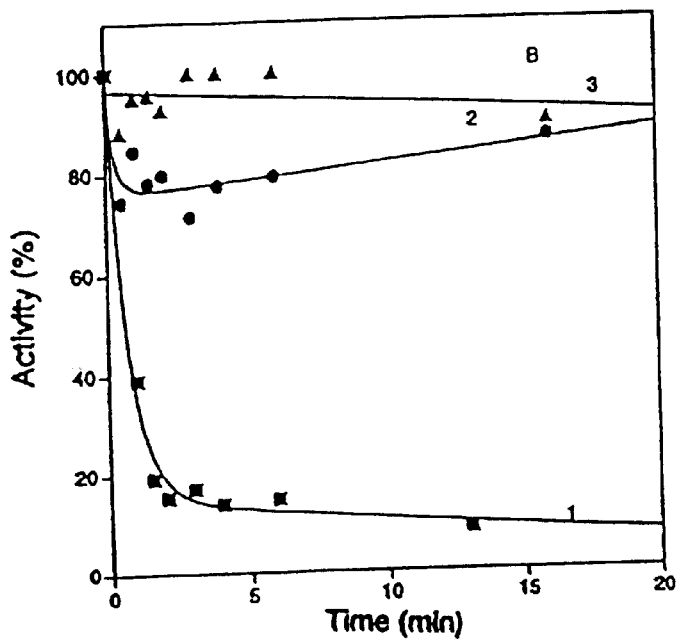

Influence of pyruvate and ThDP on the kinetics of inactivation by 2-oxo-3-alkynoic acids. With 2-oxo-3-heptynoic acid, the presence of 1 mM ThDP and 5 mM MgCl$_2$ stimulated inactivation of 3-lip PDHc and resolved E1. However in the absence of ThDP, 3-lip PDHc was still inactivated to the same extent, but at a slower rate (FIG. 2A). Pyruvate (5 mM) in the presence of 1 mM ThDP and 5 mM MgCl$_2$ failed to protect the 3-lip PDHc from inactivation. The value of $[S]_{0.5}$ for pyruvate with 3-lip PDHc in the presence of different concentrations of 2-oxo-3-heptynoic acid was 0.234±0.025 mM, not significantly different from that obtained in the absence of reagent ($[S]_{0.5}$=0.22 mM).

These results suggest that 2-oxo-3-heptynoic acid is covalently bound to an amino acid in or near the active site, rather than forming a covalent adduct with ThDP in the active center.

With 2-oxo-3-pentynoic acid at 3 mM concentration, addition of 5 mM pyruvate afforded partial protection on the slow phase of inactivation of 1-lip PDHc (21%) in the presence of 1 mM ThDP and 5 MM MgCl$_2$ (i.e. the residual activity after 26 min of inactivation was 14% in the absence and 35% in the presence of pyruvate).

With 2-oxo-3-butynoic acid, the inactivation of 1-lip PDHc and resolved E1 was ThDP-dependent, but even in the absence of ThDP, a partial inactivation of 1-lip PDHc, and to a lesser extent resolved E1, was observed (FIG. 2B presents results with E1). This could be due to the presence of some tightly bound ThDP in the active site of E1. The E1 activities measured after reconstitution with E2–E3 subcomplex, but in the absence of excess ThDP and Mg(II) in the incubation medium, were in the range of 1–15% of the activity measured in the presence of 0.2 mM ThDP and 1 mM Mg(II). Pyruvate (5 mM) in the presence of 1 mM ThDP and 5 mM MgCl$_2$ completely protected the E1 component from modification by 2-oxo-3-butynoic acid, and partially protected 1-lip PDHc (A$_t$ was 20% in the absence of pyruvate and 60% in the presence of 5 mM pyruvate), suggesting that pyruvate and 2-oxo-3-butynoic acid are bound at the same or proximal sites. The effects of different concentrations of pyruvate and 2-oxo-3-butynoic acid on the steady-state kinetics of the 1-lip and 3-lip PDHc catalyzed reactions were analogous to those observed with 2-oxo-3-heptynoic acid: the V$_{max}$ for 3-lip PDHC decreased, but the [S]$_{0.5}$ for pyruvate was almost unchanged after treatment with 2-oxo-3-butynoic acid (0.262±0.069 mM) relative to 0.22 mM. This suggests that 2-oxo-3-butynoic acid is either a non-competitive (reversible) or irreversible inhibitor of PDHc.

Tests for reversibility of inactivation. It was shown for all three 2-oxo-3-alkynoic acids that once inactivated, the 1-lip and 3-lip PDH complexes did not regain any activity, even after extensive dialysis for 15 h against 20 mM KH$_2$PO$_4$ buffer, pH 7.5 (data not shown). Nor was activity regained with totally inactive 3-lip PDHc (A$_r$=0) or partially inactivated enzyme (A$_r$=59%), after gel-filtration through a Sephadex G-25 column (PD-2, Pharmacia). Finally, there was no restoration of activity to 99.62% inactivated (with 2-oxo-3-butynoic acid) 3-lip PDHc after 20-fold dilution and incubation for 50 min in a mixture containing all components necessary for the overall reaction. All of these experiments suggest that the analogs cause irreversible inactivation.

Figure 3:
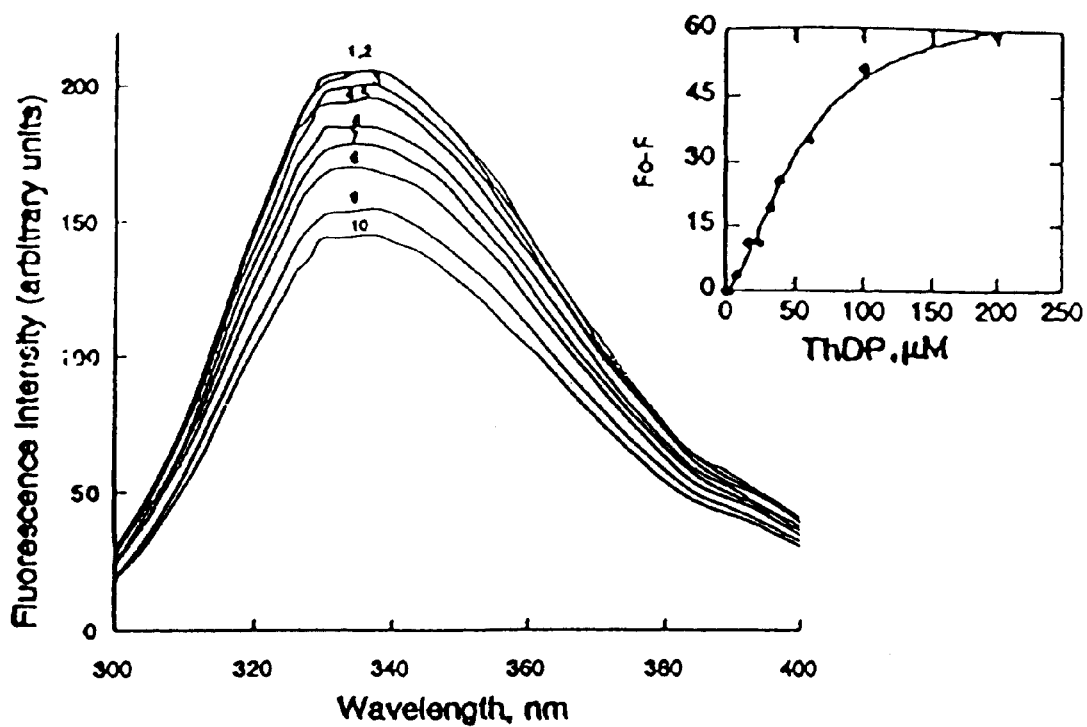
FIG. 3. Effect of ThDP on the fluorescence emission spectrum of resolved E1. The fluorescence emission spectrum of E1 (0.05 mg/mL) in 3 mL of 20 mM $KH_2PO_4$ buffer, pH 7.5, containing 1 mM $MgCl_2$ (curve 1) and the following concentrations of ThDP (curve number in parentheses): 4 $\mu$M (2); 8 $\mu$M (3); 16 $\mu$M (4); 24 $\mu$M (5); 32 $\mu$M (6); 40 $\mu$M (7); 60 $\mu$M (8); 100 $\mu$M (9) and 200 $\mu$M (10). The inset shows the dependence of the fluorescence decrease ($F_o$-F) at 335 nm on ThDP concentration, where $F_o$ is the fluorescence intensity of E1 in the absence of ThDP; F, the fluorescence intensity in the presence of the indicated concentration of ThDP.
Figure 4:
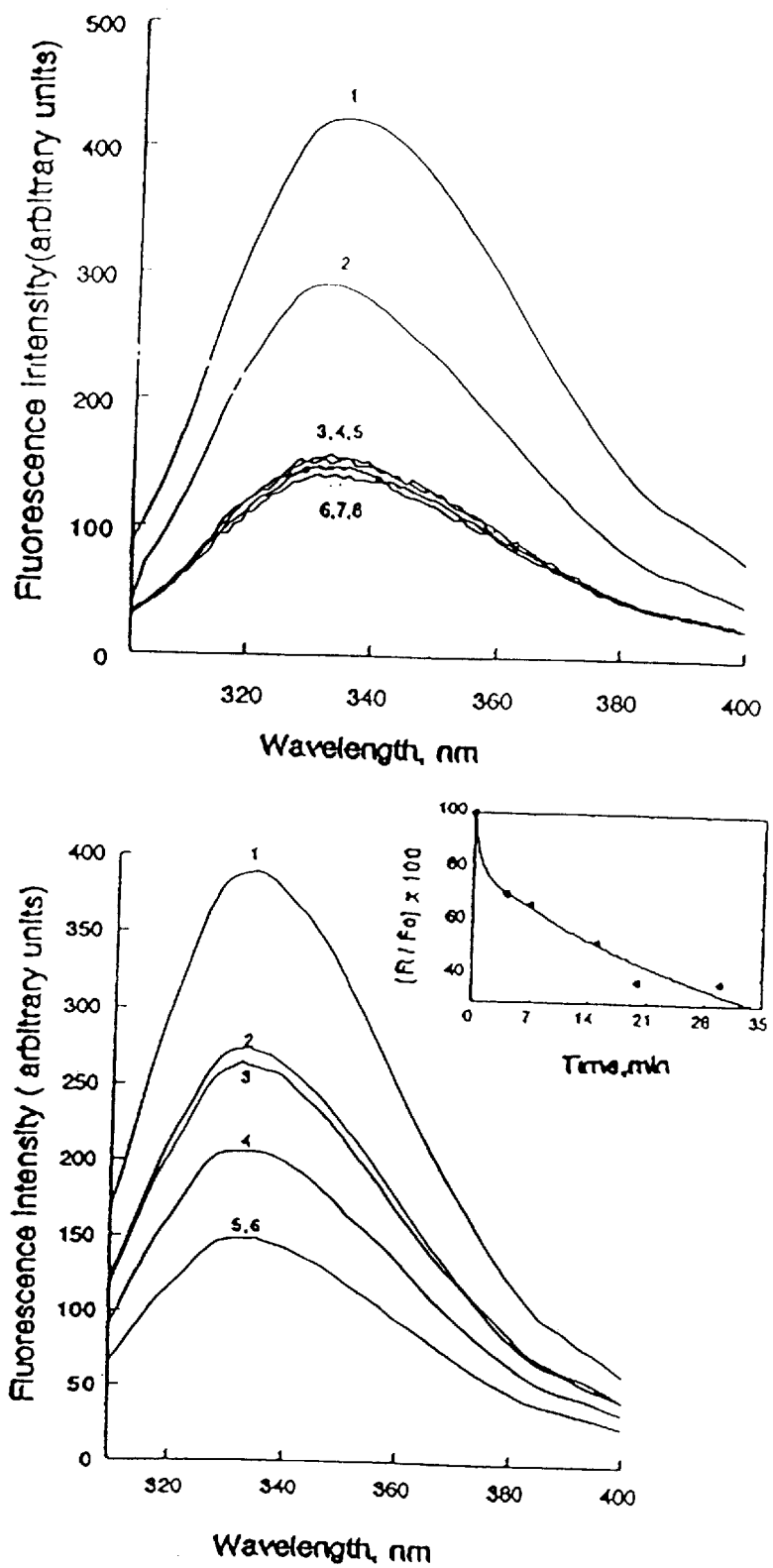
FIG. 4.

Fluorescence studies on the binding of 2-oxo-3-butynoic acid to E1. The PDHc of *E. coli* has an intrinsic fluorescence, probably due to tryptophan, which diminishes upon reconstitution with ThDP in the presence and absence of pyruvate (Henning et al., 1996). Here it was shown for the first time with resolved El that ThDP decreased the intrinsic fluorescence intensity at 335 nm (FIG. 3). The degree of fluorescence quenching was related to the ThDP concentration and the behavior indicates saturation (FIG. 3, inset), analogous to that reported for the PDH complex (Henning et al., 1996). The extent of quenching was independent of the time of preincubation with E1. Addition of pyruvate (2 mM) to E1 in the presence of ThDP (0.2 mM) and MgCl$_2$ (1 mM) decreased the fluorescence intensity by about 15%, compared to a 21% decrease in the absence of ThDP, indicating that pyruvate by itself, or in the presence of ThDP, does not induce any significant changes in the fluorescence intensity of E1 (data not shown). Adding 2-oxo-3-butynoic acid (0.11 mm) to E1 (0.173 mg/ml) in the presence of ThDP (0.2 mM) and MgCl$_2$ (1 mM), decreased the fluorescence intensity of E1 at 335 nm about 66% (FIG. 4A; the relative fluorescence in the presence of 2-oxo-3-butynoic acid was calculated with respect to curve 2 in FIG. 4A). It was shown that the 66% decrease of the intrinsic fluorescence in the presence of 2-oxo-3-butynoic acid is achieved during the first 5 min of incubation and does not change significantly after prolonged incubation with the inhibitor (FIG. 4A). This behavior is consistent with the kinetic data shown in FIGS. 1A and 1B. The decrease in fluorescence intensity depends on the concentration of 2-oxo-3-butynoic acid added (about 35% decrease in the presence of 0.033 mM, and 66% in the presence of 0.1 mM inhibitor, respectively). In the absence of added ThDP time-dependent changes in fluorescence intensity were observed (FIG. 4B and inset). The curve presented in the inset (FIG. 4B) shows a biphasic decrease of the fluorescence intensity: the short fast phase may be due to tightly bound ThDP, and the slower phase might be due to nonspecific binding of 2-oxo-3-butynoic acid near the active site. The first-order rate constant of fluorescence intensity decrease was 0.042 min$^{-1}$ for the slow phase, as compared with k=0.69 min$^{-1}$ for inactivation of PDHc, and 1.73 min$^{-1}$ for inactivation of E1 in the presence of 0.11 mM 2-oxo-3-butynoic acid. A parallel experiment in which the E1 activity was measured under conditions closely resembling those used for fluorescence analysis, revealed that significant inactivation of the enzyme by 2-oxo-3-butynoic acid only occurs in the presence of ThDP (residual activity was 40%). This correlates with a 66% quenching of the fluorescence of E1 in the presence of ThDP. In the absence of added ThDP, the residual activity of E1 was 78–90%. These results suggest that changes in fluorescence intensity induced by 2-oxo-3-butynoic acid in the absence of ThDP reflect non-specific binding of the inhibitor near the active site.

Figure 5:
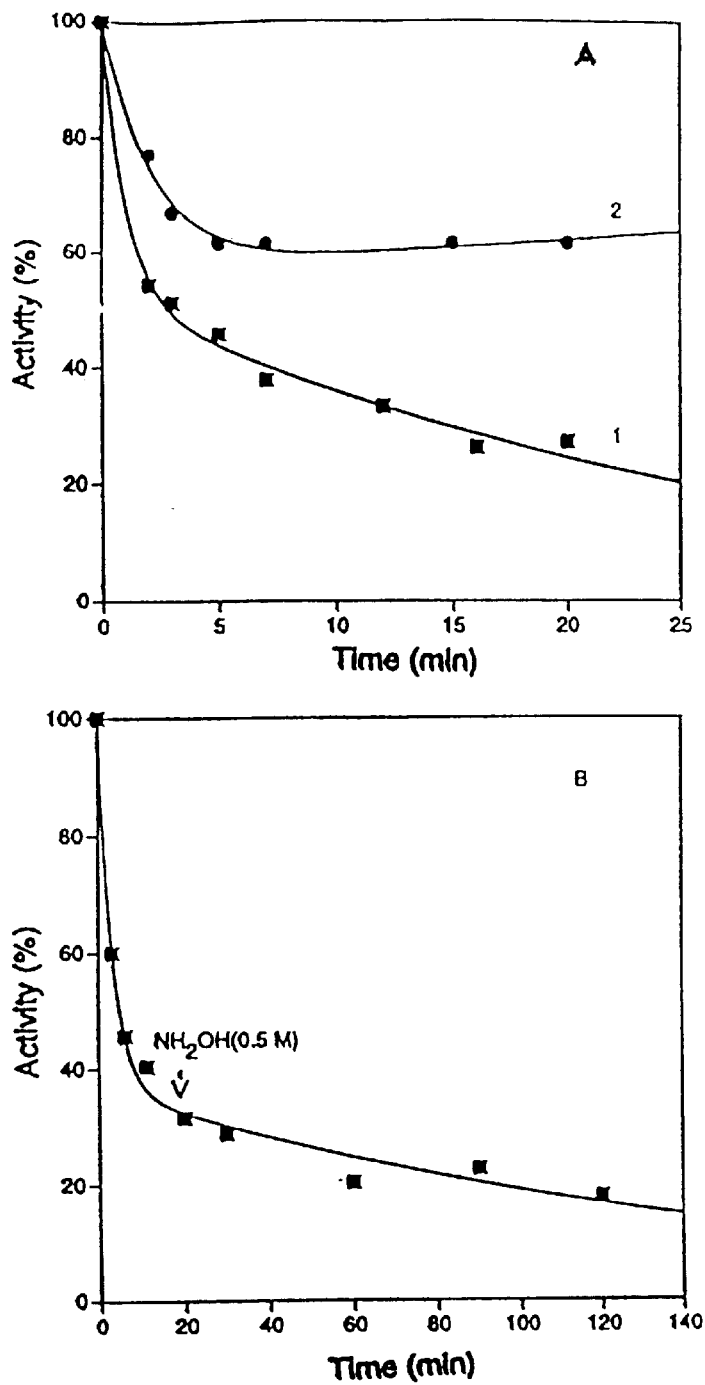
FIG. 5.

Protection from inactivation by DTT and attempted reactivation by hydroxylamine. DTT at 5 mM concentration afforded partial protection from inactivation of E1 by 2-oxo-3-butynoic acid (FIG. 5A) and of 3-lip PDHc by 2-oxo-3-heptynoic acid (data not presented). The residual activity of E1 treated for 15 min with 0.5 mM 2-oxo-3-butynoic acid was about 30% in the absence, and 63% in the presence of 5 mM DTT. However, addition of 5 mM DTT to previously inactivated E1 (A$_r$=30%) caused a modest reactivation of enzyme, A$_r$=40% after 60 min (data not shown). This suggests that DTT reacts with 2-oxo-3-butynoic acid, but can also rescue some of the inactivated enzyme. This further implies that SH-groups on the enzyme might be involved in the inactivation process. Hydroxylamine added to partially inactivated enzyme at concentrations of 0.2, 0.5 and 1 M at neutral pH failed to restore activity after 100 min (FIG. 5B), or even after 15 h, thereby excluding the formation of an acyl thioester linkage during the inactivation.

Quantification of sulfhydryl groups of E1 reacted with 2-oxo-3-butynoic acid. To investigate whether inactivation of E1 is accompanied by modification of SH-groups, the sulfhydryl contents of active E1 and E1 treated with 2-oxo-3-butynoic acid, were determined. Under denaturing but non-reducing conditions (8 M urea), 5.13 SH-groups per E1 monomer were titrated with DTNB. This agrees very closely with published values: 5.1 (Vogel, 1971); 6.2 (Flournoy & Frey, 1989); 5.6 (Lowe & Perham, 1984); and the presence of 6 cysteine residues in the DNA-derived primary structure (Stephens et al., 1983a), and on the basis of amino acid composition (Dennert & Eaker, 1970) of the E1 subunit (molecular mass=99,474). When E1 was reacted with 2-oxo-3-butynoic acid to a residual activity of 10%, and re-purified by G-25 chromatography (PD-2, Pharmacia) to remove excess reagent, DTNB titration showed that 3.83±0.18 SH-groups remain per monomer. This indicates that inactivation of E1 by 2-oxo-3-butynoic acid is accompanied by specific modification of 1.3 SH-groups per monomer (5.1–3.8).

Figure 6:
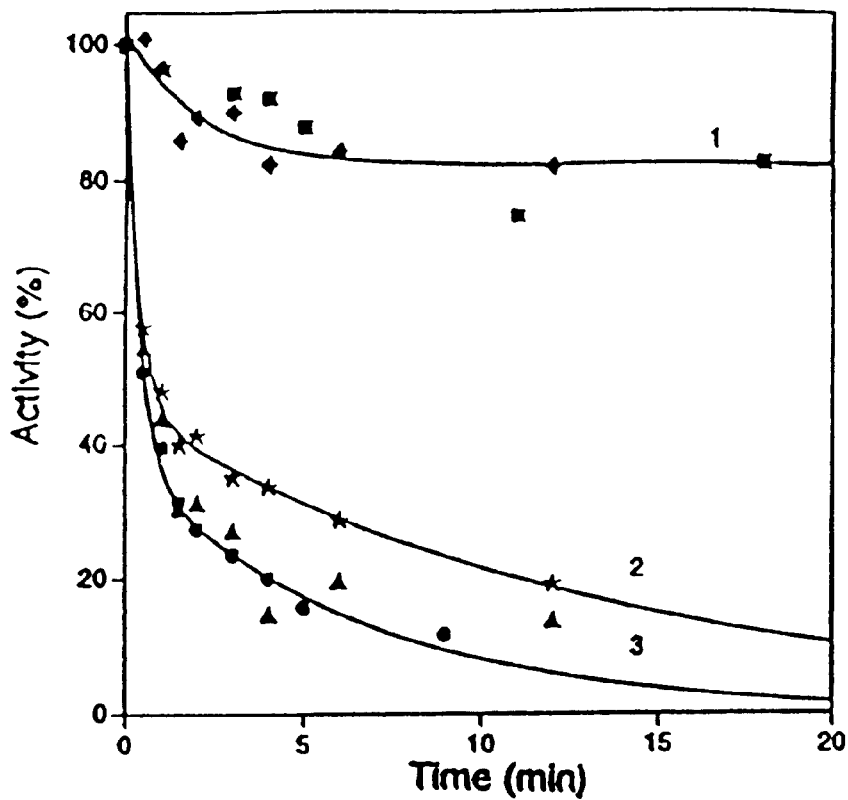
FIG. 6. Inactivation of 1-lip PDHc and its C259N and C259S variants by 2-oxo-3-butynoic acid. 1-lip PDHc (0.162 mg/mL) or the C259N and C259S variants of 1-lip PDHc (0.162 mg/mL) in 20 mM $KH_2PO_4$ buffer, pH 7.5, containing 1 mM ThDP and 5 mM $MgCl_2$ were incubated in the absence (curve 1: 1-lip PDHc and C259N variant) or in the presence of 1 mM of 2-oxo-3-butynoic acid (curve 2: the C259N variant; curve 3: 1-lip PDHc and the C259S variant) in a total volume 0.5 mL in the dark. At different times, aliquots of 50 $\mu$L were withdrawn and the overall activity was measured as described in FIG. 1A.

Inactivation of C259N and C259S variants of 1-lip PDHc by 2-oxo-3-butynoic acid. It was previously shown (Yi et al., 1996) that substituting Cys259 in the ThDP-binding fold by asparagine (C259N) or serine (C259S) yields proteins with 58% and 27% of parental 1-lip PDHc activity, respectively. However, it would appear that Cys259 is not required for inactivation by 2-oxo-3-butynoic acid because both variants were inactivated by this compound (FIG. 6). Fluoropyruvate likewise inactivated both variants, as well as the parental complexes, and resolved E1 (data not shown).

Reaction of 2-oxo-3-alkynoic acids with pyruvate oxidase. The interaction between the three pyruvate analogs and pyruvate oxidase from *Lactobacillus plantarum* showed that the $k_{app}$ vs. [I] plots with 2-oxo-3-heptynoic acid and 2-oxo-3-pentynoic acid curved upward at higher inhibitor concentration, indicating that the enzyme was not being saturated by the inhibitor. Rather, it appears that there are two reactive sites, such that reaction at the first site makes the second more accessible. On the other hand, inhibition by 2-oxo-3-butynoic acid, appeared to proceed with saturation, indicating that this compound behaves like a substrate (see Table 3). Of the three compounds 2-oxo-3-butynoic acid is therefore the most effective inhibitor of POX, PDHc, and resolved E1.

TABLE III

Kinetic constants for the inactivation of PDC and POX by 2-oxo-3-alkynoic acids.

| Enzyme/ Inhibitors | $k_i$ (min$^{-1}$) | $K_{i,c}$ (mM) | $K_{i,r}$ (mM) | $k_c/K_{i,c}$ (min$^{-1}$ mM$^{-1}$) | saturation by inhibitor |
|---|---|---|---|---|---|
| PDC 2-Oxo-3-butynoic acid | 0.0844 | 2.11 | | 0.0400 | no |
| PDC 2-Oxo-3-heptynoic acid[a] | 0.603 | 0.447 | 0.921 | 1.35 | yes |
| PDC (+50 mM pyruvamide) 2-Oxo-3-heptynoic acid[a] | 0.314 | 0.0597 | 0.382 | 5.26 | yes |
| POX 2-Oxo-3-butynoic acid | 0.268 | 0.951 | | 0.282 | yes |
| POX 2-Oxo-3-pentynoic acid[b] | | | | 0.00284[c] 0.0124[d] | no |
| POX 2-Oxo-3-heptynoic acid[b] | | | | 0.00369[c] 0.0192[d] | no |

[a]Exhibits biphasic double reciprocal plots of $1/k_{app}$ vs. $1/[I]$ and can be treated with equations assuming two-site inhibition as in Kuo & Jordan (1983). $K_{i,c}$ and $k_i$ refer to one site, $K_{i,r}$ to the second site, c and r mean catalytic and regulatory.
[b]Exhibit upward curvature of $k_{app}$ vs. [I] plots and the data are obtained from linear portions at low (c) and high inhibitor concentrations (d). Reaction of 2-oxo-3-alkynoic acids with pyruvate decarboxylase.

2-Oxo-3-butynoic acid and 2-oxo-3-heptynoic acid behaved very differently with PDC (Table 3). The 4-carbon compound gave relatively weak inactivation ($k_i/K_i$=0.04 mM$^{-1}$ min$^{-1}$) and did not appear to saturate the enzyme. However, the 7-carbon acid appeared to be a potent inhibitor ($k_i/K_i$= 1.35 mM$^{-1}$ min$^{-1}$), and its effect was significantly increased on addition of 50 mM pyruvamide ($k_i/K_i$=5.26 mM$^{-1}$ min$^{-1}$), a substrate surrogate that cannot be decarboxylated but converts PDC to its activated form (Hübner et al., 1978).

Another peculiar feature observed only with the 7-carbon analog, was the biphasic nature of the double-reciprocal plots for $k_{app}$ vs. [I]. This was previously observed with compounds in the 2-oxo-4-phenyl-3-butenoic acid class, where it was interpreted as evidence for two-site inactivation (Kuo & Jordan, 1983); the data presented in Table 3 were calculated using the same analysis. It is clear from Table 3, of the enzymes tested, pyruvate decarboxylase is least sensitive to inactivation with 2-oxo-3-butynoic acid.

Discussion

2-Oxo-3-alkynoic acids with 4-, 5- and 7-carbon chains were synthesized as potential inhibitors for pyruvate decarboxylating enzymes. The inhibitory properties of these compounds were investigated vis-à-vis three ThDP-dependent enzymes: PDHc and resolved E1 from *E. coli*; PDC from *Saccharomyces cerevisiae*; and POX from *Lactobacillus plantarum*. The 4-carbon parent compound 2-oxo-3-butynoic acid exhibited the greatest potency towards PDHc. The preference for the shorter carbon chain is consistent with results of Bisswanger (1981) who showed that the affinity of 2-oxoacids for *E. coli* PDHc decreases with increasing carbon chain length, 2-oxobutanoic acid being the only homologue to serve as a substrate ($K_m$=3 mM). The following conclusions were drawn from detailed studies on the inactivation of this complex and its E1 component by the three compounds.

1. 2-Oxo-3-butynoic acid acts as an active-site directed inhibitor of PDHc because: (a) the inactivation is ThDP-dependent; (b) pyruvate protects the enzyme from inactivation; and (c) the value of $K_i$ is 7.9 µM for PDHc and 8.5 µM for E1, significantly smaller than the $K_m$ for pyruvate (0.22 mM).

2. The binding of 2-oxo-3-butynoic acid near the active site of E1 was confirmed by fluorescence spectroscopy. Only in the presence of saturating concentrations of ThDP and MgCl$_2$ were specific changes induced in the fluorescence intensity of E1. However, additional non-specific binding of the compound near the active center is also possible. These data do not contradict earlier data indicating that pyruvate can bind in the absence of ThDP, but at site(s) different from the catalytic site (Shepherd & Hammes, 1976; Moe & Hammes, 1984; Bantel-Schaal & Bisswanger, 1980). Likewise, it has been reported that the reaction of *E. coli* PDHc with the pyruvate analog acetylphosphinate in the presence of ThDP and MgCl$_2$ decreases the fluorescence intensity by 30% in a time-dependent manner compared with only 6% for 2 mM pyruvate (Schonbrunn-Hanebeck et al., 1990). The acetylphosphinate induced decrease in fluorescence was dependent on ThDP and MgCl$_2$, reflecting the slow transformation of the E.I complex to inactive enzyme.

3. The kinetics of inactivation of PDHc and E1 by 2-oxo-3-butynoic acid is complex. The plots of activity remaining versus time were biphasic. In the presence of high concentrations of 2-oxo-3-butynoic acid a second slower phase of inactivation was found not to vary significantly with inhibitor concentration, suggesting that the additional step/steps may be involved in the inactivation of enzyme. In the presence of small concentrations of inhibitor the fast inactivation phase was followed by a steady-state level, suggesting that the inhibitor concentration decreased due to substrate-like turnover, however additional experiments would be required to prove this. These results differ from data presented by Flournoy and Frey (1989) for inactivation of PDHc and E1 by fluoropyruvate. In that case, increasing the concentration of fluoropyruvate from 0.03 to 0.6 mM decreased the rate constants of inactivation and the enzyme was protected from inactivation. The results were explained invoking a benzoin-type condensation, which was observed when the E1 component was incubated with pyruvate in the absence of CoA and NAD$^+$ or other electron acceptors. Similar behavior was noted for the inactivation of E1 by bromopyruvate (Lowe & Perham, 1984).

4. The respective second-order rate constants for inactivation of PDHc and resolved E1 (Table 1) are $104 \times 10^3$ M$^{-1}$ min$^{-1}$ and $210 \times 10^3$ M$^{-1}$ min$^{-1}$ for 2-oxo-3-butynoic acid compared to $10 \times 10^3$ M$^{-1}$min$^{-1}$ and $13 \times 10^3$ M$^{-1}$min$^{-1}$ for fluoropyruvate (presented in Table 1 and calculated from data of Flournoy & Frey, 1989). The $K_i$ values for 2-oxo-3-butynoic acid are 7.9 $\mu$M with 1-lip PDHc and 8.5 $\mu$M with resolved E1, compared to 90±15 $\mu$M for the reversible inhibition of resolved E1 by bromopyruvate (detected using the dichorophenolindophenol assay, see Lowe & Perham, 1984). The kinetic data suggest that 2-oxo-3-butynoic acid is the most powerful inhibitor of the three substrate analogs.

5. Inactivation of E1 by 2-oxo-3-butynoic acid is accompanied by the specific modification of 1.30±0.35 SH-groups per subunit, compared to 1.37±0.03 with fluoropyruvate and 1.2±0.3 with bromopyruvate. These results unambiguously show that a reactive SH group of E1 is involved in all three inactivation reactions. Inactivation of PDHc and resolved E1 by fluoropyruvate is accompanied by the acetylation of a reactive cysteine by 2-acetyl-ThDP which is formed in the active site of E1 during the decarboxylation of fluoropyruvate and elimination of fluoride ion (Flournoy & Frey, 1989). A similar inactivation mechanism was proposed for bromopyruvate with resolved E1 (Lowe & Perham, 1984).

However, the mechanism of inhibition of PDHc by bromopyruvate is different from that with fluoropyruvate. It was proposed that bromopyruvate is decarboxylated at the active site of E1, followed by reductive bromoacetylation of E2 (Lowe & Perham, 1984). Bromopyruvate then reacts with the free remaining thiol groups of the lipoic acid residues resulting in the inactivation of PDHc. For the following reasons, it seems unlikely that inhibition of 1-lip PDHc by 2-oxo-3-butynoic acid is accompanied by inactivation of E2 as with bromopyruvate: (1) The rate of inhibition by bromopyruvate was significantly increased in the presence of pyruvate. However, in the case of 2-oxo-3-butynoic acid , pyruvate partially protected the 1-lip PDHc against the inactivation; (2) The failure to reactivate 2-oxo-3-butynoic acid-treated E1 (FIG. 5B) and 3-lip PDHc treated by 2-oxo-3-heptynoic acid (data not shown) by prolonged incubation with hydroxylamine excludes the formation of a thioester bond; (3) The values of $K_i$ presented in Table 1 for PDHc (0.0079 mM) and resolved E1 (0.0085 mM) are very similar to each other and suggest that inhibition of PDHc activity is accompanied primarily by inactivation of E1.

It is also unlikely that inactivation is due to formation of a hemithioketal between a cysteine sulfhydryl group and the ketone functionality, since such reactions are highly reversible (Torchinsky, 1977). Furthermore, it was shown that the catalytic activity of E1 is not significantly affected by reaction with 5,5'-dithiobis-(2-nitrobenzoic acid), or methylmethanethiolsulfonate (data not shown). A 300-fold molar excess of p-chloromercuribenzoate was required to inactivate E1, suggesting that the reactive cysteine is deeply buried. It seems more likely that a Michael-type adduct is formed by adding a cysteine SH across the triple bond. Further experiments with labeled 2-oxo-3-butynoic acid would be required to confirm this possibility. There is evidence for such an interaction between PDC and E-4(4-chlorophenyl)-2-oxo-3-butenoic acid and related compounds (Kuo & Jordan, 1983; Jordan et al., 1986; Zeng et al., 1991; Menon-Rudolph et al., 1992). Indeed, protein chemical methods were used to identify such a Michael adduct between Cys221, a residue that is responsible for substrate activation of PDC (Zeng et al., 1993; Baburina et al., 1994; Baburina, 1996; Baburina et al., 1996), and p-chlorocinnamaldehyde (derived from decarboxylation of E-4(4-chlorophenyl)-2-oxo-3-butenoic acid; see Dikdan, 1994). In addition, 2-oxo-4-phenyl-3-butynoic acid was shown to inhibit brewer's yeast PDC, and to undergo enzymatic conversion to cis and trans cinnamic acids. It would appear likely that both double- and triple-bonded pyruvate analogs readily undergo Michael additions in the presence of a suitable nucleophile on the enzyme.

6. The greater sensitivity of the overall reaction relative to the non-oxidative formation of the acetoin and acetolactate side products in the inactivated enzyme, could mean that alkylation of a single E1 monomer has less effect on the non-oxidative reaction than on oxidative acyl transfer. This further supports a crucial role of a cysteine different from Cys259 on E1, and further confirms that the inactivation takes place on E1.

Although 2-oxo-4-phenyl-3-butenoic acid and 2-oxo-4-phenyl-3-butynoic acid (Chiu & Jordan, 1994) inhibited brewer's yeast PDC, they had no effect on $E.$ $coli$ PDHc due to its high substrate specificity (Bisswanger, 1981). In contrast, PDC is less sensitive to inhibition by the 2-oxo-3-alkynoic acids than PDHc (cf. Tables 1 and 3). The preference of PDC for larger, more hydrophobic inhibitors is also evident from its greater susceptibility to inhibition by E-4(4-chlorophenyl)-2-oxo-3-butenoic acid than 2-oxo-3-butynoic acid: the respective first order rate constant of inactivation ($k_i$), $K_i$ and $k_i/K_i$ were: 0.054 min$^{-1}$, 1.1 mM and 0.049 mM$^{-1}$min$^{-1}$ for 2-oxo-3-butynoic acid compared to 0.38 min$^{-1}$ and 0.7 mM and 0.54 mM$^{-1}$min$^{-1}$ for E-4(4-chlorophenyl)-2-oxo-3-butenoic acid). It is interesting to note that comparable data have been published for another pyruvate analog, acetylphosphinate ($CH_3COPO_2H_2$) (Schonbrunn-Hanebeck et.al., 1990; Spinka & Hübner, 1996). Here a first order rate constant of 0.6 min$^{-1}$ and $K_i$=0.15 $\mu$M were observed with PDHc from $E.$ $coli$ compared with $K_i$=50 $\mu$M for POX from $Lactobacillus$ $plantarum$ and $K_i$=0.47 mM for PDC from $Saccharomyces$ $cerevisiae$, suggesting that acetylphosphinate is a poor inhibitor of PDC (Spinka & Hübner, 1996).

The rapid drop-off in inactivation efficacy with increased carbon chain length is not surprising for POX, since even 2-oxobutanoic acid fails to show substrate-like activity with this enzyme according to the manufacturer's information.

In conclusion, several new 2-oxo-3-alkynoic acids were synthesized and shown to be potent irreversible inhibitors of three ThDP-dependent pyruvate decarboxylating enzymes. The rate constants for inactivation were particularly impressive for 2-oxo-3-butynoic acid acting on the E1 component of PDHc. Indeed, this inhibitor appears to be the most potent irreversible inactivator of PDHc known. It appears to alkylate a cysteine residue close to the active center, but not Cys259 in the ThDP fold.

It is expected that the compounds of the present invention would, in addition to inhibiting the enzymes already mentioned (pyruvate dehydrogenase multienzyme complex, pyruvate oxidase and pyruvate decarboxylase), also irreversibly (in a time-dependent manner) inhibit the enzyme acetohydroxyacid synthase (AHAS, also known as acetolactate synthase).

EXAMPLE II

HERBICIDAL ACTIVITY ASSAYS

Rates of application for the compounds of this invention are determined by a number of factors. These factors include: formulation selected, method of application, amount of vegetation present, growing conditions etc. In general terms, the subject compounds should be applied at rates from 0.0005 to 20 kg/ha, with a preferred rate range from 0.001 to 0.25 kg/ha. Compounds of this invention may be used alone or in combination with other commercial herbicides, insecticides or fungicides. A combination of a compound from this invention with one or more of the herbicides listed in FIG. 7 may be particularly useful for weed control.

Herbicidal activities of the subject compounds will be assessed in greenhouse tests. Such test procedures are set forth below.

Seeds of barley (*Hordeum volgare*), barnyard grass (*Echinochloa crus-galli*) cheat grass (*Bromus secalinus*) or downy brome (*Bromus tectorum*) cocklebur (*Xanthium pensylvanicum*), corn (*Zea mays*) cotton, (*Gossypium hirsutum*), crab grass (Digitaria spp), giant foxtail (*Setaria faberi*), morningglory (Ipomoea spp), rice (*Oryza sativa*) sorghum (*Sorghum bicolor*) would be planted and treated pre-emergence with test chemicals dissolved in a non-phytotoxic solvent. At the same time, these crop and weed species would be treated with post-emergence applications of test chemicals. Plants would range in height from two to eighteen centimeters for postemergence studies. Treated plants and controls would be maintained in a greenhouse for approximately 16 days, after which all species will be compared to controls and visually evaluated. Plants would be compared assessing the following criteria: chlorosis/necrosis, growth retardation, formative effect and unusual pigmentation.

References

Adamson, S. R., & Stevenson, K. J. (1981) *Biochemistry* 20, 3418–3424.
Adamson, S. R., Robinson, J. A., & Stevenson, K. J. (1984) *Biochemistry* 23, 1269–1274.
Apfel, M. A., Ikeda, B. H., Speckhard, D. C., & Frey, P. A. (1984) *J. Biol.Chem.* 259, 2905–2909.
Annan, N., Paris, R., Jordan, F (1989) *J.Am.Chem.Soc.* 111, 8895–8901.
Baburina, I., Gao,Y., Hu.Z., Hohmann, S., Furey, W., & Jordan F. (1994) *Biochemistry* 33,5630–5635.
Baburina, I., Moore, D. J., Volkov, A., Kahyaoglu, A., Jordan, F., & Mendelsohn R. (1996) *Biochemistry* 35, 10249–10255.
Baburina, I. (1996) Ph.D. Dissertation, Rutgers University Graduate Faculty, Newark, N.J.
Bantel-Schaal, U., & Bisswanger H. (1980) Hopper-Seyler's *Z. Physiol. Chem.* 361, 1265–1266.
Bisswanger, H., & Henning, U. (1971 ) *Eur. J. Biochem.* 24, 376–384.
Bisswanger, H. (1980) *Biochem. Biophys. Res. Commun.* 95, 513–519.
Bisswanger, H. (1981) *J.Biol.Chem.* 256, 815–822.
Bremer, J. (1969 ) *Eur. J. Biochem.* 8, 535–540.
Chiu, C. C., & Jordan, F. (1994) *J. Org. Chem.* 59, 5763–5766.
Dikdan, G. (1994) Ph.D. Dissertation, Rutgers University Graduate Faculty, Newark, N.J.
Dennert, G., & Eaker, D. (1970) *FEBS Lett.* 6, 257–261.
Farrenkopf, B., & Jordan, F. (1992) *J. Protein Expression Purif.* 3, 101–107.
Flournoy, D. S., & Frey, P. A. (1989) *Biochemistry* 28, 9594–9602.
Gunsalus, I. C. (1954) in The Mechanism of Enzyme Action (McElvoy, W. D., & Glass, B., Eds.) pp 545–580, Johns Hopkins, Baltimore, Md.
Gutowski, J. A., & Lienhard, G. E. (1976) *J. Biol. Chem.* 251, 2863–2866.
de Graaf-Hess & de Kok, A. (1982) *FEBS Lett.* 143, 261–264.
Henning, J., Kern G., Neef, H., Bisswanger H., & Hübner G. (1996) in Biochemistry and Physiology of Thiamin Diphosphate Enzymes, Bisswanger, H., & Schellenberger, A. Eds. A. u. C. Intemann, Prien, Germany, pp. 235–243 Holzer, H., Shultz, G., Villar-Palasi, C., & Juntgen-Sell, J. (1956) *Biochem. Z.* 327, 331–344.
Hübner, G.; Weidhase, R.; Schellenberger, A. (1978) *Eur. J. Biochem.* 92 175–181.
Jackson, P. H., & Singer, T. P. (1983) *J. Biol. Chem.* 258,1857–1865.
Jordan, F., Adams, J., Farzami, B., Kudzin, Z. H. (1986) *J. Enz. Inhib.* 1, 139–149.
Kitz R., & Wilson I. B. (1962) *J. Biol. Chem.* 237, 3245–3249.
Koike, M., Reed, L., & Carroll, W. R. (1960) *J. Biol. Chem.* 235, 1924–1930.
Kluger, R., & Pike, D. C.(1977) *J. Am. Chem. Soc.* 99, 4504–4506.
Kuwana, H., Caroline, D. F., Harding, R. W., & Wagner, R. P. (1968) *Arch. Biochem. Biophys.* 128, 184–193.
Kuo, D. J., & Jordan F. (1983) *Biochemistry* 22, 3735–3740.
Lowe, P. N., & Perham, R. N. (1984) *Biochemistry* 23, 91–97.
Lowe, P. N., Leeper, F. J., & Perham, R. N. (1983) *Biochemistry* 22, 150–157.
Machado, R. S., Clark, D. P., & Guest, J. R. (1992) *FEMS Microbiol. Lett.* 100, 243–248.
Machado, R. S. (1993) Ph.D. Thesis, University of Sheffield.
Massey, V. (1963) in The Enzymes (Boyer, P. D., Lardy, H., & Myrback, K., Eds.) 2nd Ed, Vol 7, pp 275–305, Academic Press, New York.
Maldonado, M. E., Oh, K., & Frey, P. A. (1972) *J. Biol. Chem.* 247, 2711–2716.
Menon-Rudolph, S., Nishikawa, S., Zeng, X., Jordan, F. (1992) 114, 10110–10112.
Moe, O. A., & Hammes, G. G. (1974) *Biochemistry* 13, 2547–2552.
McNally, A. J., Motter, K., & Jordan, F. (1995) *J. Biol. Chem.* 270, 19736–19743.
Reed, L. J. (1974) *Acc. Chem. Res.* 7, 40–47.
Russell, G. C., Machado, R. S. & Guest, J. R. (1992) *Biochem. J.* 287, 611–619.
Shepherd, G. B., & Hammes, G. G. (1976) *Biochemistry* 15, 311–317.
Schwartz, E. R., Old, L. O., & Reed, L. (1968) *Biochem. Biophys. Res. Commun.* 31,495–500.
Schonbrunn-Hanebeck, E., Laber, B., & Amrhein, N. (1990) *Biochemistry* 29, 4880–4885.
Schwartz, E. R., & Reed, L. J. (1970) *Biochemistry* 9, 1434–1439.
Spinka, M., & Hübner, G. (1996) in Biochemistry and Physiology of Thiamin Diphosphate Enzymes, Bisswanger, H., & Schellenberger, A. Eds. A. u. C. Intemann, Prien, Germany, pp. 186–194.
Stephens, P. E., Darlison, M. G., Lewis, H. M., & Guest, J. R.(1983a) *Eur. J. Biochem.* 133, 155–162.
Stephens, P. E., Darlison, M. G., Lewis, H. M., & Guest, J. R.(1983b) *Eur. J. Biochem.* 133, 481–489.
Stephens, P. E., Lewis, H. M., Darlison, M. G., & Guest, J. R. (1983c) *Eur. J. Biochem.* 135, 519–527.
Stevenson, K. J., Hale, G., & Perham, R. N. (1978) *Biochemistry* 17, 2189–2192.

Torchinsky (1977) in Sulfur in Proteins (Metzler, D., Ed.) p 17, Pergamon Press, Oxford.

Vogel, O., & Henning, U (1971) *Eur.J.Biochem.* 133, 155–162.

Westerfeld, N. W. (1945) *J. Biol. Chem.* 161, 495–502.

Yi, J., Nemeria, N., McNally, A., Jordan, F., Machado, R. S., & Guest, J. R. (1996) *J. Biol. Chem.* 271, 33192–33200.

Zeng, X., Chung, A., Haran, M., & Jordan, F. (1991) *J. Amer. Chem. Soc.* 113, 5842–5849.

Zeng, X., Farrenkopf, B., Hohmann, S., Dyda, F., Furey, W., & Jordan, F. (1993) *Biochemistry* 32, 2704–2709.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A herbicidal composition comprising a herbicidally effective amount of a compound having the formula:

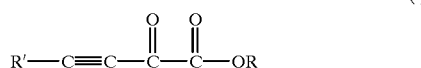

(I)

wherein R represents H or the residue of a protecting group; R' represents R" $(CH_2)_n$—, wherein R" is selected from the group consisting of hydrogen or halogen, or R' represents unsubstituted or substituted phenyl $(C_6H_5)$, wherein the phenyl substituent is at least one selected from the group consisting of fluorine or trifluoromethyl; and n is an integer from 0–4, or an agriculturally suitable salt of the acid form of said compound, and a carrier medium.

2. The composition of claim 1, wherein R is the residue of an ester protecting group which is cleavable by a plant esterase.

3. The composition of claim 2, wherein said ester protecting group is selected from the group consisting of a benzyloxymethyl ester and a methoxymethyl ester.

4. The composition of claim 1, wherein R is the residue of an ester protecting group that is photochemically cleavable.

5. The composition of claim 4, wherein said ester is a phenyl-substituted phenyacyl ester.

6. The composition of claim 1, wherein R is the residue of a t-butyl ester protecting group.

7. The composition of claim 1 wherein said carrier medium comprises an inert liquid diluent and, optionally a surfactant.

8. The composition of claim 7, wherein said liquid diluent is a solvent for the compound of formula I.

9. The composition of claim 1, wherein said carrier medium comprises an inert solid diluent.

10. The composition of claim 1, further comprising at least one additive selected from the group consisting of anti-foaming agents, anti-caking agents, anti-corrosive agents, anti-bacterial agents and anti-fungal agents.

11. A method for controlling the growth of undesired vegetation which comprises applying to the site to be protected the composition of claim 1.

12. A method for controlling the growth of undesired vegetation which comprises applying to the site to be protected the composition of claim 2.

13. A method for controlling the growth of undesired vegetation which comprises applying to the site to be protected the composition of claim 3.

14. A method for controlling the growth of undesired vegetation which comprises applying to the site to be protected the composition of claim 4.

15. A method for controlling the growth of undesired vegetation which comprises applying to the site to be protected the composition of claim 5.

16. A method for controlling the growth of undesired vegetation which comprises applying to the site to be protected the composition of claim 6.

17. A method for controlling the growth of undesired vegetation which comprises applying to the site to be protected the composition of claim 7.

18. A method for controlling the growth of undesired vegetation which comprises applying to the site to be protected the composition of claim 8.

19. A method for controlling the growth of undesired vegetation which comprises applying to the site to be protected the composition of claim 9.

20. A method for controlling the growth of undesired vegetation which comprises applying to the site to be protected the composition of claim 10.

21. A herbicidal composition as claimed in claim 1 wherein said compound is selected from the group consisting of 2-oxo-3-butynoic acid, 2-oxo-3-pentynoic acid and 2-oxo-3 heptynoic acid.

22. A herbicidal composition as claimed in claim 1, further comprising at least one herbicide selected from the group consisting of: anilofos, bensulfuron methyl, benfuresate, bentazon, benzofluor, bifenox, bromoxynil, butachlor, chlormethoxynil, chlornitrofen, cinmethylin, CGA 142464, desmetryn, dichlobenil, dimepiperate, dymron, esprocarb, ethofumesate, fenoxaprop, fluazifop, fluorodifen, fomesafen, lactofen, oxadiazon, oxyfluorfen, pendimethalin, pretilachlor, propanil, pyrazosulfuron ethyl, pyrazolate, quizalofop ethyl, quinclorac, SK-233, thiobencarb, triclopyr, 2,4-D, 2,4-DB, 1-(α,α-dimethylbenzyl)-3-p-toluylurea, 1-α,α-dimethyl-p-methylbenzyl-3-p-toluylurea, MCPA, MCPB, MON 7200, mefluidide, mefenacet, and methazole.

\* \* \* \* \*